(12) United States Patent
May

(10) Patent No.: US 8,557,293 B2
(45) Date of Patent: Oct. 15, 2013

(54) SUNSCREEN COMPOSITIONS FOR APPLICATION TO PLANTS

(76) Inventor: Scott May, Erdenheim, PA (US)

( * ) Notice: Subject to any disclaimer, the term of this patent is extended or adjusted under 35 U.S.C. 154(b) by 305 days.

(21) Appl. No.: 12/869,514

(22) Filed: Aug. 26, 2010

(65) Prior Publication Data

US 2012/0052187 A1 Mar. 1, 2012

(51) Int. Cl.
| | | |
|---|---|---|
| *A61K 9/14* | (2006.01) | |
| *A61K 31/28* | (2006.01) | |
| *A61K 31/315* | (2006.01) | |
| *A61K 31/695* | (2006.01) | |
| *A01N 59/00* | (2006.01) | |
| *A01N 59/16* | (2006.01) | |

(52) U.S. Cl.
USPC ........... 424/489; 424/617; 424/641; 424/724; 504/119; 504/120; 514/63; 514/492; 514/494

(58) Field of Classification Search
None
See application file for complete search history.

(56) References Cited

U.S. PATENT DOCUMENTS

| | | | | |
|---|---|---|---|---|
| 7,431,743 | B2 * | 10/2008 | Hughes | 8/506 |
| 8,404,263 | B2 * | 3/2013 | Ishaque et al. | 424/405 |
| 2002/0041866 | A1 * | 4/2002 | Morales et al. | 424/93.5 |
| 2008/0219938 | A1 | 9/2008 | Grune | |
| 2009/0192038 | A1 | 7/2009 | Hoobler et al. | |

FOREIGN PATENT DOCUMENTS

| | | | |
|---|---|---|---|
| DE | 19757522 | * | 7/1999 |
| WO | WO2009064450 A1 | | 5/2009 |

OTHER PUBLICATIONS

Shao & Schlossman, "Using TiO2 and ZnO for Balanced UV Protection", Annual Scientific Meeting of the Society of Cosmetic Chemists, Southwest Chapter, Aug. 28, 2008, available at : http://www.koboproductsinc.com/Downloads/SWSCC-Yun-Poster-02.pdf last accessed on Sep. 24, 2010.

Shao & Schlossman, "Effect of Particle Size on Performance of Physical Sunscreen Formulas", Presentation at PCIA Conference, Shanghai China, Mar. 1999, pp. 1-9, available at: http://www.koboproductsinc.com/Downloads/PCIA99-Sunscreen.pdf last accessed on Sep. 24, 2010.

* cited by examiner

*Primary Examiner* — Alton Pryor
(74) *Attorney, Agent, or Firm* — Howard IP Law Group, PC

(57) ABSTRACT

A sunscreen composition for application for plants comprises Titanium Dioxide ($TiO_2$), Zinc Oxide (ZnO), Silicon Dioxide ($SiO_2$), a surfactant, wetting agent, dispersant (SWD) and water. The composition forms a suspension concentrate when combined that when diluted in water provides a solution that provides uniform coverage using convention spraying equipment. A method of protecting plants including turfgrass from ultraviolet radiation, heat stress and/or sunburn comprises combining $TiO_2$, ZnO, $SiO_2$, SWD and water to form a suspension concentrate. The suspension concentrate is then diluted in water and applied to an area in which sun protection is desired.

23 Claims, No Drawings

SUNSCREEN COMPOSITIONS FOR APPLICATION TO PLANTS

FIELD OF THE INVENTION

The present invention relates to sunscreen compositions. More particularly, the present invention relates to sunscreen compositions applicable to plants such as turfgrass.

BACKGROUND OF THE INVENTION

Plants are living organisms many of which rely on the sun to survive. Green plants capture the energy of sun and convert the sunlight into energy to sustain the plant through the process of photosynthesis. Plants have many uses including food, medicines and other non-food products, as well as aesthetic uses such as lawns, turf, gardens and the like. Plant species are cultivated to provide shade, modify temperatures, reduce wind and noise, provide privacy and prevent soil erosion. Lawn grasses, shade trees, ornamental trees, shrubs, vines, herbs, perennials and bedding plants are frequently used to beautify outdoor gardens. Sports such as football, soccer, baseball and golf are performed on grass surfaces.

The effects of harmful radiation from the sun are well known. Exposure to ultra-violet (UV) radiation can damage the skin and deteriorate certain materials through extended exposure to sunlight containing the UV spectrum. In the case of skin, the protective layer of skin may burn or blister causing painful and possibly irreversible damage. In extreme cases of prolonged exposure, permanent damage such as skin cancer may develop. Sunscreens have been developed to help mitigate the damages from UV radiation. Sunscreens may take the form of lotions, gels, oils among other formulae that may be applied to the skin and reflect or absorb light in the UV spectrum, thus preventing the UV radiation from penetrating the skin. Plants and other forms of life are also susceptible to the harmful effects of the sun. In particular, plants are adversely affected by the UV radiation emitted by the sun, as well as the heat generated from the sun's radiation.

The ultra-violet spectrum (wavelength of 100-400 nanometers (nm)) is comprised of UV-C (100-280 nm), UV-B (280-313 nm) and UV-A (315-400 nm) radiation. UV-B radiation in particular may have significant photo-biological effects, causing modifications to the biological and biochemical environment of the plant. Radiation may affect a plant by direct destruction of the DNA at a molecular level, disruption of cell membranes or other cell structures, and may inhibit various physiological functions, for example, photosynthesis, nutrient assimilation and chlorophyll and protein synthesis which may result in reduced growth and development of the plant.

An example where the damage of UV radiation to plants is acutely evident is with regard to cultivated turfgrass. Cultivated turfgrass may be used in locations such as golf courses, ball fields, parks and botanical gardens. Over the area of the typical golf course, for example, different grass heights are maintained for different types of play and leisure activities. In some areas, for example, putting greens, it is desirable to have a ball move rapidly across the surface during play. To achieve this, turfgrass on greens may be maintained at blade lengths of ⅛ inch (in.) or less. With such small blade lengths, the effects of heat and radiation are magnified and require measures be taken to prevent damage or possibly death of the turfgrass.

Golf courses and other institutional users of turfgrass must supply water to the affected turfgrass in an amount sufficient to provide adequate cooling. This however, requires significant manpower and water resources. In many areas, water resources are strictly monitored and rationed due to water shortages. This results is high costs for labor and irrigation and contributes to shortages of valuable water resources. It would be beneficial to have a composition to provide UV protection from the sun and can be spread uniformly and over a wide area of the terrain.

SUMMARY OF THE INVENTION

A composition comprising titanium dioxide ($TiO_2$), zinc oxide (ZnO), silicon dioxide ($SiO_2$), a surfactant, wetting, dispersant agent (SWD) and a pigment are suspended in a suspension concentrate for use as sun protection for plants, for example, turfgrass. A dilute solution using the composition is suitable for application using conventional spraying equipment such as a backpack sprayer or a boom sprayer. The $TiO_2$ and ZnO, in combination form an aggregate composed of varying sized particles resulting in enhanced sun protective properties. The particles are suspended in such a way that they are evenly dispersed throughout the composition and thus provide even coverage when sprayed. The composition protects the plant through it's high refractive index and attenuation of ultra violet radiation resulting in less plant damage from drought, heat stress, and sunburn.

DETAILED DESCRIPTION OF THE EMBODIMENTS

When used in this specification, the term exemplary should be given the meaning of representative or serving as an illustration or specimen. Use of the term exemplary should not be construed to indicate any other status such as preferred, commendable, worthy of imitation, or the like.

By shielding a plant, for example, turfgrass from harmful ultra-violet (UV) radiation, the health and vitality of the plant may be dramatically improved. The rate of photosynthesis in plants is directly affected by temperature. For example, when turfgrass reaches a temperature of about 84° F., the turfgrass plant shuts down, stopping photosynthesis until the temperature again drops into an acceptable range. Water in the soil is used by the plant in an attempt to regulate the leaf temperature. However, in situations where there is inadequate water available to compensate for the high temperature, the plant goes dormant. Dormancy is observable in browning of turfgrass and the cessation of growth. In the context of a household lawn, the turfgrass browns and remains that way until the temperature drops, or sufficient water is applied through watering or rainfall at which time the turfgrass revives itself, becoming green and continuing to grow.

In turfgrass applications such as a golf course however, dormancy of the turfgrass creates additional problems. First, the aesthetics of brown turfgrass at a finely groomed golf course is unacceptable to most customers utilizing the course. The additional pressure of pedestrian and cart traffic on the turfgrass contributes to further damage, as the turfgrass cannot grow and regenerate itself. Once the turfgrass is damaged by traffic, it may not grow back, causing the permanent damage to be particularly evident. Common types of turfgrass used in golf courses include but are not limited to Kentucky Bluegrass, Bentgrass, Ryegrass, Bermuda grass, Fescue and the like.

By way of non-limiting example, the composition may be used on ryegrass. Ryegrass is a popular choice for turfgrass because of its ability to rapidly produce thick, durable turf. One of the world's most widely used grasses, Ryegrass possesses the ability to germinate in as little as 7 to 10 days. Being a cool season grass, ryegrass is commonly used in Northern regions, or is used to overseed dormant grass during the winter months in hotter regions, such as the Southern United States. Ryegrass produces dark green turf with a strong root system and is resistant to some diseases which frequently affect other grasses like bluegrass. Ryegrass thrives in a variety of soil types and even grows well in clay and compacted areas. When the composition is applied to the turf canopy (the distance between the soil and the tip of the blade of turfgrass) of ryegrass, the UV blocking properties of the composition protect the ryegrass from sun damage and help produce healthy vibrant turfgrass.

Certain compositions have traditionally been used in an attempt to shield plants from the damaging effects of the sun. The main ingredients of these conventional compositions have been calcium carbonate (limestone) or kaolin clay. These products act to create a thick film over the plant or fruit to prevent insect damage (e.g. in the case of kaolin clay) and sun damage. Compositions that use limestone preparations are very high in pH. As a result, such compositions are not suitable for turfgrass where high pH conditions are undesirable, in that among other things, high pH environments facilitate fungal diseases. Additionally, these materials are highly soluble in water, and tend to wash off the plant surface when it rains. Furthermore, the film created by kaolin clay applications is not suitable for turfgrass for aesthetic reasons, as the clay changes the color of the turfgrass to the reddish brown color of the clay.

An embodiment of the composition provides exceptional sun blocking characteristics when applied to the surfaces of plants, such as turfgrass. In an embodiment, the composition comprises the following: $TiO_2$, ZnO, $SiO_2$, a surfactant/wetting/dispersant agent (SWD), and a pigment. Combined with a small amount of water, this produces a suspension concentrate. The suspension concentrate may be diluted in water to be used for example, in a sprayer and applied to an affected area. The proportion of $TiO_2$ may be a range of about 15%-35% by weight composition with an exemplary proportion of about 27% by weight. The proportion of ZnO may be in a range of 6%-17% by weight composition, in an embodiment about 9% by weight. In a exemplary embodiment, the ratio by weight composition of $TiO_2$ to ZnO is between about 3:1 to 5:1. The proportion of SWD may be in the range of 15%-35% by weight composition with an exemplary proportion of about 27% by weight. $SiO_2$ is present in a proportion by weight composition in the range of 5%-25% with an exemplary proportion of about 18% by weight.

Due to the white color of the $TiO_2$ and the ZnO, a pigment with a proportion composition of about 6% by weight may be added. The amount of pigment may be adapted so as to impart a color in the blue or green hues and produce a desired color of turfgrass upon application. For example, in an exemplary embodiment, the pigment may include a copper compound to impart a blue-green hue. The remainder of the composition is water, for example, in a proportion of about 9.5% by weight.

The properties of the individual components are be described herein.

Titanium dioxide ($TiO_2$) occurs in nature, most commonly in a form known as rutile, a very stable form of $TiO_2$. Rutile has one of the highest refractive indices of any known material. A high refractive index attenuates UV radiation from the sun, redirecting the radiation as it passes through the $TiO_2$. $TiO_2$ has strong UV absorbing capabilities that along with its high refractive index provide very high UV protection. Additionally, $TiO_2$ is also stable and not subject to discoloration under UV light. Further, $TiO_2$ is a photo-catalyst under UV light. When exposed to UV light, valence electrons in the $TiO_2$ are released causing surface oxidation which serves to eliminate potentially harmful organic substances such as bacteria and fungi. The anti-microbial characteristics of $TiO_2$ as a photo catalyst may protect turfgrass from harmful bacterial or fungal infections in addition to its sun blocking properties.

Zinc oxide (ZnO), like $TiO_2$ has a high refractive index and also exhibits anti-bacterial properties. ZnO in the presence of water produces Hydrogen Peroxide when exposed to UV light. Both ZnO and $TiO_2$ are opaque and white in color and often used as white pigments. Therefore, according to an embodiment, the composition includes a pigment to compensate for the opacity of the $TiO_2$ and the ZnO. The particle size of ZnO affects the wavelength at which absorption characteristics are maximized. Thus, the use of a variety of particle sizes in an aggregate form and the tandem use of $TiO_2$ and ZnO provide broad protection across the entire UV spectrum.

Silicon dioxide ($SiO_2$) promotes plant health through the formation of a thick silicated epidermal cell layer that maintains erect leaves and enhances photosynthesis. $SiO_2$, also known as silica, is the most abundant mineral in the Earth's crust. Silica is absorbed into the plant's epidemic layer and promotes resistance to pests through the formation of a thick cuticle silicon layer. Silica helps reduce water losses to transpiration and thereby increases the plant's ability to regulate its temperature.

As described above, $TiO_2$ has high opacity and a white color. ZnO is slightly less opaque than $TiO_2$ but still is characterized by a white color. For this reason, application of $TiO_2$ and ZnO to plants, for example, turfgrass leaves the plants with a white appearance. A pigment is added to the composition so that application of the composition to the plant, for example, turfgrass provides the plant with a natural color appearance. In one embodiment, the pigment is generally blue with some green pigments and is obtained copper compounds.

In order to get the particles of $SiO_2$, ZnO, and $SiO_2$ to remain in suspension, a surfactant, wetting agent and dispersant (SWD) is used. A surfactant or wetting agent is a substance that lowers the surface tension of a liquid and lowers the interfacial tension between two different liquids. A SWD is utilized as part of the composition so the particles of $TiO_2$, ZnO, and $SiO_2$ form a suspended solution preventing sedimentation and clumping. A surfactant allows the bonding of a non-aqueous substance like ZnO to be combined in solution thereby facilitating even spreading and stable suspension in solution. A dispersant or dispersing agent is added to a solution to improve the separation of particles and to prevent settling and clumping. By way of a non-limiting example, AU-330L, manufactured by Adjuvants Unlimited of Tulsa, Okla. may be used as a SWD.

The $TiO_2$, ZnO, and $SiO_2$ begin as granules with particle sizes, for example, in the range of about 0.5 to 1 mm. Smaller particles create dust while mixing and tend to reduce the operational lifetime of spraying equipment and risk the health of operators who must handle the materials and may breathe in dust from the dry raw materials. The use of granules reduces the dust created during the mixing process and produces the aggregate of particle sizes that provide the widest range of UV protection. The SWD maintains the aggregate particles in solution which keeps them sufficiently mixed for effective application to the turfgrass. If sedimentation or clumping occurs, the resulting composition does not fit through a nozzle in a sprayer. Therefore, it is important to maintain the particles in a solution. Such clumping, may cause non-uniform flow through the nozzle of a sprayer, resulting in uneven application to the turfgrass. In more severe circumstances, clumping may result in a fouled or clogged nozzle, further reducing the equipment's operational capacity and overall lifetime.

The sunscreen composition described herein is effective at improving the health and vitality of turfgrass exposed to heat stress and overexposure to the sun's UV radiation. Due to its consistency, the composition is dispersed uniformly via conventional spraying equipment and provides even protection over the spraying area and provides the synergistic advantageous properties provided by all the ingredients. When test sprayed on areas of turfgrass during times of extreme heat and sunlight, turfgrass covered with the composition exhibited vibrant healthy grass compared to control areas that were not treated with the composition.

In an embodiment of the sunscreen composition, a suspension concentrate is formed consisting of $TiO_2$, ZnO, $SiO_2$, a pigment, water, and a SWD. The $TiO_2$ is added in a proportion of about 30.12 percent by weight. The ZnO is added in a proportion of about 9.04 percent by weight. $SiO_2$ is added in a proportion of about 18.07 percent by weight. A pigment is added to adapt the sunscreen composition to the color of the turf to be treated such that the pigment makes up a proportion of the sunscreen composition at about 6.02 percent by weight. A SWD is added to form a proportion of about 27.10 percent by weight. Finally, water is added in a proportion of about 9.65 percent by weight. According to this embodiment, an amount of suspension concentrate sufficient to cover one acre may be prepared by combining 0.80 pounds (lbs) of water, 2.25 lbs of SWD, 2.50 lbs of $TiO_2$, 0.75 lbs of ZnO, 1.50 pounds of $SiO_2$ and 0.5 lbs of pigment.

The suspension concentrate is diluted in water to form a sunscreen solution. The sunscreen solution may then be applied to an area containing plants to be protected in a conventional manner such as a sprayer. The sunscreen solution when sprayed provides an even dispersion of particles providing effective protection from heat stress and sunburn.

In accordance with an embodiment of the composition, a sunscreen for application to plants including turfgrass, is formed by combining in dry form, $TiO_2$ in an amount representing from about 10% to about 45% by weight of the composition. The $TiO_2$ may be comprised of particles having particle sizes of about 0.5 millimeters (mm) to about 1.0 mm. ZnO is added to the $TiO_2$ in a dry form such that the ZnO make up about 6% to about 17% of the composition by weight. The ZnO may likewise be comprised of particles with particle sizes of about 0.5 millimeters (mm) to about 1.0 mm. In an exemplary embodiment, the ratio of $TiO_2$ to ZnO in the composition by weight is about 3:1 to about 5:1. Added to the combined dry $TiO_2$ and the dry ZnO, $SiO_2$ is added in a dry form such that the $SiO_2$ comprises from about 10% to about 30% of the composition by weight. The combined $TiO_2$, ZnO, and $SiO_2$ are then mixed with a SWD. The SWD is a liquid, for example, AU-330L, a SWD manufactured by Adjuvants Unlimited of Tulsa Okla. may be used as the SWD according to an embodiment of the composition. The SWD may constitute from about 15% to about 35% of the composition by weight. The dry $TiO_2$, ZnO and $SiO_2$ along with the SWD are combined with water at a percentage by weight of about 9% of the composition. The $TiO_2$, ZnO, $SiO_2$, SWD and water may further be combined with a pigment adapted to match a natural color of the turfgrass to which it is applied. A pigment added to the composition may make up about 6% of the composition by weight. The combined components are then mixed in accordance with chemical mixing techniques well known in the art. The resultant composition is a suspension concentrate. The suspension concentrate may be mixed with an amount of water to produce a sunscreen solution adapted to provide UV protection from the sun and be spread uniformly and over a wide area of the terrain.

The sunscreen solution may then be applied to a plant, such as turfgrass by methods commonly employed in the art, such as convention high-volume hydraulic sprayer, low volume sprayers, ultra-low volume sprays, pressurized liquid injection and like. The relative amounts applied to turfgrass such as ryegrass, is about 1.7 ounces (oz.) to about 3.4 oz. per 1,000 sq. ft. In an embodiment, the first application of the composition may be performed prior to the onset of heat or sun stress or when the temperature exceeds 80° F. The composition may be applied every 7 to 21 days depending on the rate used, existing weather conditions and the growth rate of the turfgrass. A lower application interval may be used when conditions of low humidity and intense sun are forecasted. It is desirable to provide continuous and uniform coverage is maintained to improve the health of treated turfgrass. Tests performed on areas treated with the composition of this embodiment show increased growth rate and vitality of the treated turfgrass. Other benefits are documented based on the use of an embodiment of the composition. In a test on mature creeping bentgrass with a fairway height stand, compositions containing Titanium, Zinc and an embodiment of the composition were applied to test plots of bentgrass along with test plots treated with the commercial fungicide DACONIL brand of chlorothalomil and compared to an untreated control to observe the effect of the treatments on Dollar Spot, a fungal disease that affects many varieties of turfgrasses infected by the fungus *Sclerotinia homeocarpa*. Test plots were rated as to Dollar Spot severity, turfgrass color and overall turfgrass quality. The test was conducted at a time when dollar spot pressure was severe and the level of turfgrass quality was low due to Dollar Spot blighting. Dollar Spot severity was reduced in all treatments compared with the untreated control. The commercial fungicide resulted in the highest turfgrass quality rating followed by an embodiment of the composition which performed better than either the Ti or Zn alone. Testing thus shows that in addition to the sun screening characteristics of the composition, the additional benefit of fungal disease control is provided by the composition.

In testing, an embodiment of the composition consisting of $TiO_2$ in a proportion of about 30.12 percent by weight, ZnO in a proportion of about 9.04 percent by weight, $SiO_2$ in a proportion of about 18.07 percent by weight, a pigment in a proportion of about 6.02 percent by weight, a SWD in a proportion of about 27.10 percent by weight, and water in a proportion of about 9.65 was applied to five 5 cm×5 cm poly methyl methacrylate (PMMA) plates. An additional 5 cm×5 cm PMMA plate was left untreated. Each plate was placed over an integrating sphere aperture of a double monochromator spectroradiometer and irradiated with a solar simulator. The spectral irradiance at wavelengths from 250-800 nm was measured at 1 nm intervals for each plate treated with the composition as well as the untreated plate. A transmission, $T_\lambda$ of the composition at each wavelength was computed as the ratio of spectral irradiance transmitted by each substrate, with and without the embodiment of the composition. An average value of $1-T_{80}$ for each test treatment was computed as the percentage screened. Based on the test, the composition screened 76% of the solar energy in the ultraviolet spectrum relative to the untreated plate. Furthermore, the composition screened 82% of visible solar energy and 14% of near infrared solar energy.

The above provides a detailed description of a sunscreen composition according to various embodiments of the described composition. This description is provided by way of example only and is not intended to be limiting in any way. The scope of the present invention is limited only by the accompanying set of claims.

What is claimed is:

1. A sunscreen composition for use on plants comprising:
   titanium dioxide ($TiO_2$);
   zinc oxide (ZnO);
   silicon dioxide ($SiO_2$); and
   a surfactant, wetting agent dispersant (SWD);
   wherein the $TiO_2$ is in an amount of about 10% to about 45% $TiO_2$ by weight composition, and wherein the composition is effective in protecting plants from ultraviolet radiation damage.

2. The sunscreen composition of claim 1, wherein the ratio of $TiO_2$ to ZnO is from about 3:1 to about 5:1 by weight.

3. The sunscreen composition of claim 1, further comprising a pigment.

4. The sunscreen composition of claim 3, wherein the pigment is adapted to match a natural color of the plants.

5. The sunscreen composition of claim 3, wherein said pigment is a copper compound.

6. The sunscreen composition of claim 1, comprising from about 6% to about 17% ZnO by weight.

7. The sunscreen composition of claim 1, comprising from about 5% to about 35% $SiO_2$ by weight.

8. The sunscreen composition of claim 1, comprising from about 15% to about 35% SWD by weight.

9. The sunscreen composition of claim 1, further comprising about 10% water by weight.

10. The sunscreen composition of claim 3, comprising about 6% of said pigment by weight.

11. The sunscreen composition of claim 1, wherein said $TiO_2$ is in the form of a particulate aggregate having a plurality of particle sizes.

12. The sunscreen composition of claim 1, wherein said ZnO is in the form of a particulate aggregate having a plurality of particle sizes.

13. The sunscreen composition of claim 1, comprising about 30.12% $TiO_2$ by weight.

14. The sunscreen composition of claim 1, comprising about 9.04% ZnO by weight.

15. The sunscreen composition of claim 1, comprising about 18.07% $SiO_2$ by weight.

16. The sunscreen composition of claim 2, comprising about 27.10% SWD by weight.

17. The method of claim 16, wherein concentrated sunscreen composition further comprises a pigment, said pigment in an amount of about 6% by weight.

18. The method of claim 16, wherein said $TiO_2$ is in the form of a particulate aggregate having a plurality of particle sizes.

19. The method of claim 16, wherein said ZnO is in the form of a particulate aggregate having a plurality of particle sizes.

20. A method of protecting turfgrass from heat stress, sunburn or ultraviolet radiation comprising the steps of:
   diluting a concentrated sunscreen composition comprising:
      from about 10% water by weight
      from about 10% to about 45% titanium dioxide ($TiO_2$) by weight;
      from about 6% to about 17% zinc oxide (ZnO) by weight;
      from about 5% to about 35% silicon dioxide ($SiO_2$) by weight;
      from about 15% to about 35% surfactant, wetting agent, dispersant (SWD) by weight;
      wherein the diluting is performed by mixing the concentrated sunscreen composition with an equal part water; and
   spraying said diluted sunscreen composition on an area of turfgrass in an amount sufficient to cover the turf canopy to thereby protect the applied area of turfgrass from heat stress, sunburn or ultraviolet radiation damage.

21. A sunscreen composition for use on plants consisting of:
   water;
   titanium dioxide ($TiO_2$);
   zinc oxide (ZnO);
   silicon dioxide ($SiO_2$);
   a surfactant, wetting agent dispersant (SWD); and
   a pigment,
   wherein the $TiO_2$ is in an amount of about 10% to about 45% $TiO_2$ by weight composition, and wherein the composition is effective in protecting plants from ultraviolet radiation damage.

22. The composition of claim 21, wherein, the $TiO_2$, ZnO, and $SiO_2$ are comprised of particles having particle sizes of about 0.5 millimeters (mm) to about 1.0 mm.

23. The composition of claim 21, wherein the ratio of $TiO_2$ to ZnO is from about 3:1 to about 5:1 by weight; and wherein $SiO_2$ is present in a proportion by weight composition in the range of 5%-25%.

* * * * *

UNITED STATES PATENT AND TRADEMARK OFFICE
CERTIFICATE OF CORRECTION

PATENT NO. : 8,557,293 B2  
APPLICATION NO. : 12/869514  
DATED : October 15, 2013  
INVENTOR(S) : Scott May It is certified that error appears in the above-identified patent and that said Letters Patent is hereby corrected as shown below:

In the Claims:

Column 8, line 7, Claim 20 is renumbered as independent claim --17--;
Claim 17 is renumbered as claim --18-- and should read "The method of claim 17";
Column 7, line 46 of claim 17, now renumbered claim 18, insert --the-- after the word "therein" and before the word "concentrated";
Column 8, line 1, Claim 18 is renumbered as claim --19-- and should read "The method of claim 17";
Column 8, line 4, Claim 19 is renumbered as claim --20-- and should read "The method of claim 17".

Signed and Sealed this
Twenty-eighth Day of January, 2014

Michelle K. Lee
*Deputy Director of the United States Patent and Trademark Office*